(12) United States Patent
Villavicencio et al.

(10) Patent No.: US 11,918,820 B2
(45) Date of Patent: Mar. 5, 2024

(54) LEADLESS BIOSTIMULATOR HAVING OVERMOLDED HEADER ASSEMBLY

(71) Applicant: Pacesetter, Inc., Sylmar, CA (US)

(72) Inventors: Brett C. Villavicencio, Valencia, CA (US); Gintare Kerezyte, Moorpark, CA (US); Wesley Alleman, Santa Clarita, CA (US); Kavous Sahabi, Winnetka, CA (US)

(73) Assignee: PACESETTER, INC., Sylmar, CA (US)

( * ) Notice: Subject to any disclaimer, the term of this patent is extended or adjusted under 35 U.S.C. 154(b) by 144 days.

(21) Appl. No.: 17/153,645

(22) Filed: Jan. 20, 2021

(65) Prior Publication Data

US 2021/0220657 A1 Jul. 22, 2021

Related U.S. Application Data

(60) Provisional application No. 62/963,827, filed on Jan. 21, 2020.

(51) Int. Cl.
*A61N 1/375* (2006.01)
*A61N 1/05* (2006.01)
*A61N 1/362* (2006.01)

(52) U.S. Cl.
CPC ......... *A61N 1/37518* (2017.08); *A61N 1/362* (2013.01); *A61N 1/37512* (2017.08); *A61N 1/3754* (2013.01); *A61N 1/3756* (2013.01)

(58) Field of Classification Search
None
See application file for complete search history.

(56) References Cited

U.S. PATENT DOCUMENTS

| | | | |
|---|---|---|---|
| 4,243,042 | A | 1/1981 | Ware |
| 6,622,046 | B2 | 9/2003 | Fraley et al. |
| 6,852,925 | B2 | 2/2005 | Wolf et al. |
| 8,509,921 | B2 | 8/2013 | Doerr |
| 8,519,280 | B2 | 8/2013 | Teske |
| 9,345,185 | B2 | 5/2016 | Prasannakumar et al. |
| 9,844,659 | B2 | 12/2017 | Grubac et al. |
| 2015/0116053 | A1 | 4/2015 | Stevenson et al. |
| 2017/0113032 | A1 | 4/2017 | Sontheimer |
| 2017/0294250 | A1 | 10/2017 | Giese |
| 2018/0280685 | A1 | 10/2018 | Toy et al. |
| 2018/0339131 | A1* | 11/2018 | Muse ................ A61M 25/0102 |

(Continued)

*Primary Examiner* — Erica S Lee
(74) *Attorney, Agent, or Firm* — Womble Bond Dickinson (US) LLP (57) ABSTRACT

A leadless biostimulator, such as a leadless cardiac pacemaker, having a header assembly that includes overmolded components, is described. The header assembly includes a helix mount overmolded on a flange of an electrical feedthrough assembly. A fixation element is mounted on the helix mount. The overmolded helix mount fills a recess in an outer surface of the flange to robustly join the header assembly components. The electrical feedthrough assembly includes an electrode contained within the flange to deliver electrical impulses to a target anatomy, and an insulator that separates the electrode from the flange. The overmolded helix mount can conform or adhere to the outer surfaces of the flange and the insulator to electrically isolate the electrode from the flange. Other embodiments are also described and claimed.

20 Claims, 6 Drawing Sheets

(56) References Cited

U.S. PATENT DOCUMENTS

2019/0076664 A1* 3/2019 Ollivier .............. A61N 1/37518
2019/0366082 A1* 12/2019 Schmidt ............... A61N 1/0587
2020/0094048 A1* 3/2020 Regnier ................ A61B 5/283
2020/0129763 A1 4/2020 Paspa et al.

* cited by examiner

LEADLESS BIOSTIMULATOR HAVING OVERMOLDED HEADER ASSEMBLY

This application claims the benefit of priority of U.S. Provisional Patent Application No. 62/963,827, filed on Jan. 21, 2020, which is incorporated herein by reference in its entirety to provide continuity of disclosure.

BACKGROUND

Field

The present disclosure relates to biostimulators having header assemblies. More specifically, the present disclosure relates to leadless biostimulators having header assemblies that include an electrical feedthrough assembly and a helix mount, and methods of manufacturing such header assemblies.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The pulse generator usually connects to the proximal end of one or more implanted leads through a feedthrough assembly, which creates an isolated electrical pass-through into a hermetic case for pulse/sense transmissions to a target tissue. The feedthrough assembly can be used in low voltage or high voltage applications. A distal end of the implanted leads, which typically have lengths of 50 to 70 centimeters, contains one or more electrodes for positioning adjacent to the inside or outside wall of a cardiac chamber. The leads have an insulated electrical conductor or conductors for connecting the pulse generator to the electrodes in the heart. Accordingly, the pulse generator can deliver a pacing pulse from within a hermetically sealed housing through the feedthrough assembly, the lead, and the electrode to the target tissue.

Conventional pacemakers have several drawbacks, including a risk of lead or feedthrough assembly breakage, complex connections between the leads and the feedthrough assembly, and a risk of infection and morbidity due to the separate leads and pulse generator components. Many of the issues associated with conventional pacemakers are resolved by the development of a self-contained and self-sustainable biostimulator, or so-called leadless biostimulator. The leadless biostimulator can be attached to tissue within a dynamic environment, e.g., within a chamber of a beating heart, to deliver pacing pulses directly to the tissue without the use of leads.

SUMMARY

Existing leadless biostimulators have a hermetically sealed device package containing internal components to generate pacing pulses. The device package can have a header assembly that supports the device at a target site using a fixation element, such as a fixation helix. The fixation helix can be mounted on a helix mount of the header assembly. More particularly, the fixation helix is screwed onto a holding thread of the helix mount, which in turn is screwed onto a thread of a feedthrough assembly. The holding thread of the helix mount and the thread of the feedthrough assembly can be machined. Existing leadless biostimulators may provide electrical isolation between components of the feedthrough assembly using gaskets or adhesives. The gaskets and adhesives are additional components, having respective costs and assembly complexities, as well as potential electrical or mechanical failure pathways. Accordingly, existing leadless biostimulators can benefit from a header assembly that includes fewer manufacturing processes or components to reduce cost and increase mechanical stability and electrical reliability.

A leadless biostimulator having a header assembly including overmolded components is described. In an embodiment, the header assembly includes an electrical feedthrough assembly having a flange. The flange includes a mounting wall extending from a shoulder, and an outer surface of the mounting wall includes a recess extending around a longitudinal axis. The header assembly includes a helix mount overmolded on the flange such that the helix mount fills the recess. Accordingly, the helix mount is securely retained on the flange. For example, the helix mount can be retained on the flange via an interference between the material filling the recess and a surface of the mounting wall that defines the recess.

The outer surface of the mounting wall can be threadless. The mounting wall may, however, have non-threaded features to define the recess. For example, the mounting wall can include a neck extending distally from the shoulder to a collar, and the collar, the neck, and the shoulder can define the recess as a circumferential groove around the neck. The circumferential groove can be longitudinally between the collar and the shoulder. A depth of the recess can vary. For example, the recess can increase in depth in a proximal direction from the collar toward the shoulder. Accordingly, the mounting wall can include channels or recesses, not between threads, for the helix mount to stably grip.

The header assembly can include an electrode within a central channel of the mounting wall, and an insulator. The insulator can include an insulator wall extending between the electrode and the mounting wall. The insulator can also include a sealing collar extending radially outward from the insulator wall, e.g., from a distal insulator end. The sealing collar can at least partly cover a distal end of the mounting wall. Furthermore, the helix mount can conform to a top surface of the sealing collar. Accordingly, the helix mount overmolded on and around the insulator can electrically isolate the electrode from the mounting wall.

In an embodiment, the header assembly includes a fixation element mounted on the helix mount. For example, the fixation element can include a helix revolving about the longitudinal axis. The fixation element may be at least partly embedded within the helix mount. Accordingly, the fixation element can be secured relative to the helix mount, which is in turn secured relative to the mounting wall.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of implementations of the present disclosure are set forth with particularity in the claims that follow. A better understanding of the features and advantages of such implementations will be obtained by reference to the following detailed description that sets forth illustrative examples in which the principles of the disclosure are utilized, and the accompanying drawings of which:

DETAILED DESCRIPTION

Implementations of the present disclosure include a biostimulator, e.g., a leadless cardiac pacemaker, having a header assembly that includes overmolded components. The biostimulator may be used to pace cardiac tissue. The biostimulator may be used in other applications, however, such as deep brain stimulation. Thus, reference to the biostimulator as being a cardiac pacemaker is not limiting.

Descriptions of various implementations of the present disclosure are made with reference to the figures. However, certain implementations may be practiced without one or more of these specific details, or in combination with other known methods and configurations. In the following description, numerous specific details are set forth, such as specific configurations, dimensions, and processes, in order to provide a thorough understanding of the example implementations. In other instances, well-known processes and manufacturing techniques have not been described in particular detail in order to not unnecessarily obscure the description. Reference throughout this specification to "one implementation," "an implementation," or the like, means that a particular feature, structure, configuration, or characteristic described is included in at least one implementation. Thus, the appearance of the phrase "one implementation," "an implementation," or the like, in various places throughout this specification are not necessarily referring to the same implementation. Furthermore, the particular features, structures, configurations, or characteristics may be combined in any suitable manner in one or more implementations.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various implementations below.

In an aspect of the present disclosure, a leadless biostimulator including a header assembly having a helix mount overmolded on an electrical feedthrough assembly is provided. The overmolded construction directly integrates the header assembly components to provide good mechanical and electrical performance using few parts. The overmolded helix mount material can adhere to the electrical feedthrough assembly material to provide robust mechanical stability. The electrical feedthrough assembly can include an electrode to transmit a pacing impulse, and an insulator to electrically insulate the electrode from a flange that the helix mount is overmolded on. The overmolded helix mount can conform and adhere to the flange and the insulator to electrically isolate the components from the electrode. Thus, the overmolded construction uses few parts and a cost-effective manufacturing process to achieve robust mechanical stability and reliable electrical performance.

Figure 1:
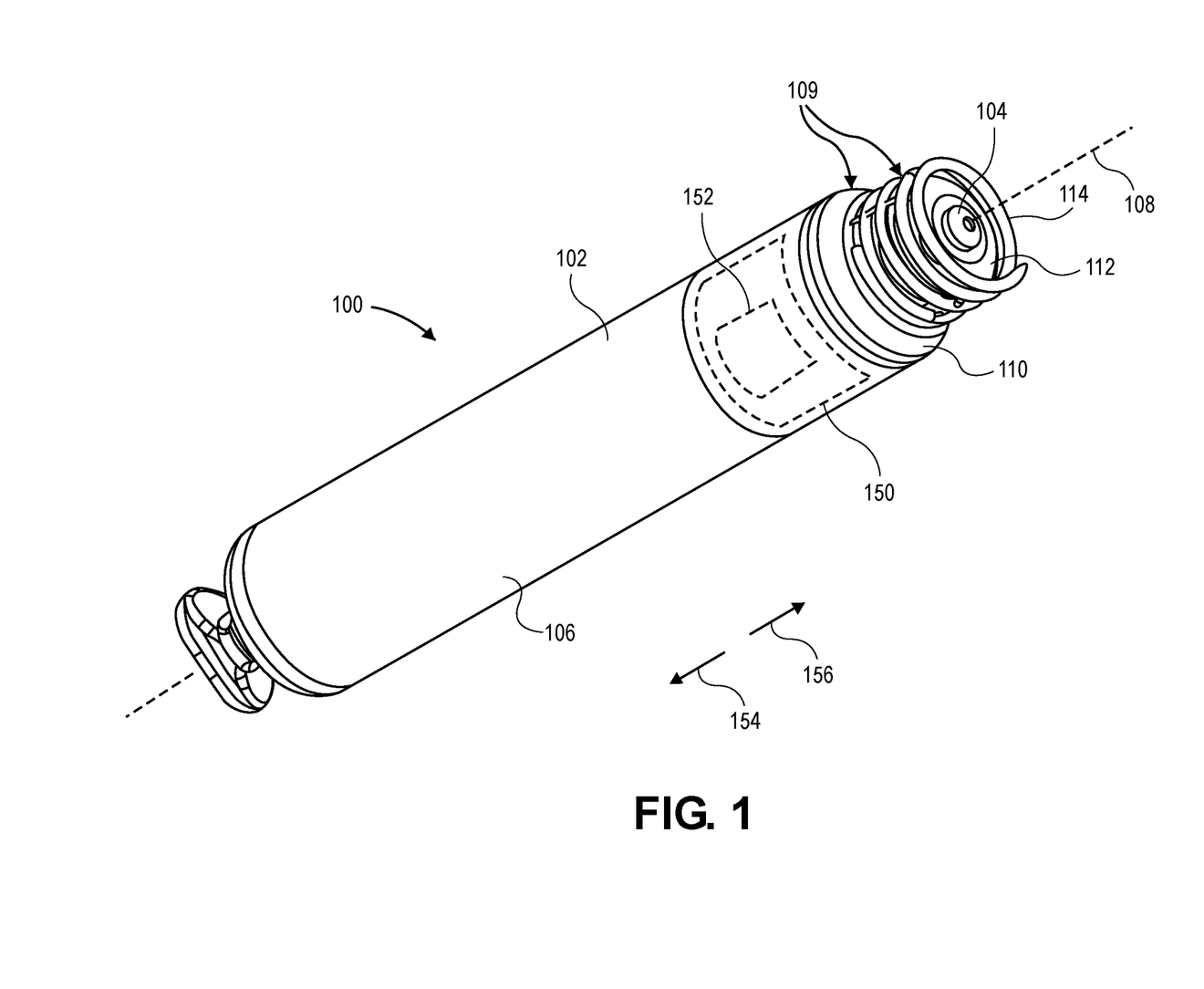
FIG. 1 is a perspective view of a leadless biostimulator, in accordance with an embodiment.

Referring to FIG. 1, a perspective view of a leadless biostimulator is shown in accordance with an embodiment. The biostimulator 100 can be a leadless biostimulator, e.g., a leadless cardiac pacemaker. The biostimulator 100 can include a housing 102 having pacing electrodes. For example, the biostimulator 100 includes each of a distal electrode 104 and a proximal electrode 106 disposed on or integrated into the housing 102. The electrodes 104, 106 can be integral to the housing 102 or connected to the housing, e.g., at a distance of less than several centimeters from the housing 102. The housing 102 can contain an energy source (not shown) to provide power to the pacing electrodes. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The housing 102 can have a longitudinal axis 108, which may be an axis of symmetry along which several other biostimulator components are disposed. For example, a header assembly 109 can be mounted on a distal end of the housing 102 along the longitudinal axis 108. The header assembly 109 can include an electrical feedthrough assembly 110, a helix mount 112 mounted on the electrical feedthrough assembly 110, and a fixation element 114 mounted on the helix mount 112. As described below, one or more of the header assembly components can be overmolded during assembly. For example, the helix mount 112 can be overmolded (from a polymer such as polyetheretherketone (PEEK), epoxy, polysulfone, polyetherimide, tecothane, elastane, or pellethane) directly on a flange of the electrical feedthrough assembly 110. The assembled components of the header assembly 109 can provide a distal region of the biostimulator 100 that attaches to a target tissue, e.g., via engagement of the fixation element 114 with the target tissue. The distal region can deliver a pacing impulse to the target tissue, e.g., via the distal electrode 104 that is held against the target tissue.

The housing 102 can have an electronics compartment 150 (shown by hidden lines). More particularly, the electronics compartment 150 can be a cavity laterally surrounded by a housing wall, e.g., a cylindrical wall, extending around the longitudinal axis 108. The housing wall can include a conductive, biocompatible, inert, and anodically safe material such as titanium, 316L stainless steel, or other similar materials, to laterally enclose the electronics compartment 150 between the energy source of the biostimulator 100 within a proximal portion of the housing 102, and the header assembly 109 at the distal portion of the biostimulator 100. More particularly, an energy source container can proximally enclose the electronics compartment 150 and the electrical feedthrough assembly 110 can distally enclose the electronics compartment. The electrical feedthrough assembly 110, the housing wall, and the power source container can surround a volume of the electronics compartment 150.

In one implementation, an electronics assembly 152 (shown by hidden lines) is mounted in the electronics compartment 150. The electronics assembly 152 can include, without limitation, a flexible circuit or a printed circuit board having one or more electronic components mounted on a substrate. For example, the electronics assembly 152 can include one or more processors, capacitors, etc., interconnected by electrical traces, vias, or other electrical connectors. In one implementation, the electronics assembly 152 includes an electrical connector to connect to the electrical feedthrough assembly 110. For example, the electrical connector can be a socket connector to receive an electrode pin of the electrode 104 (FIG. 2).

The biostimulator components, e.g., the energy source container, the electronics compartment 150 containing the electronics assembly 152, and the header assembly 109, can be arranged on the longitudinal axis 108. Accordingly, each component can extend along the longitudinal axis 108 and have a respective axial location relative to another component along the longitudinal axis 108. For example, the energy source container can be offset from the electronics compartment 150 in a proximal direction 154 and the header assembly 109 can be offset from the electronics compartment 150 in a distal direction 156.

Figure 2:
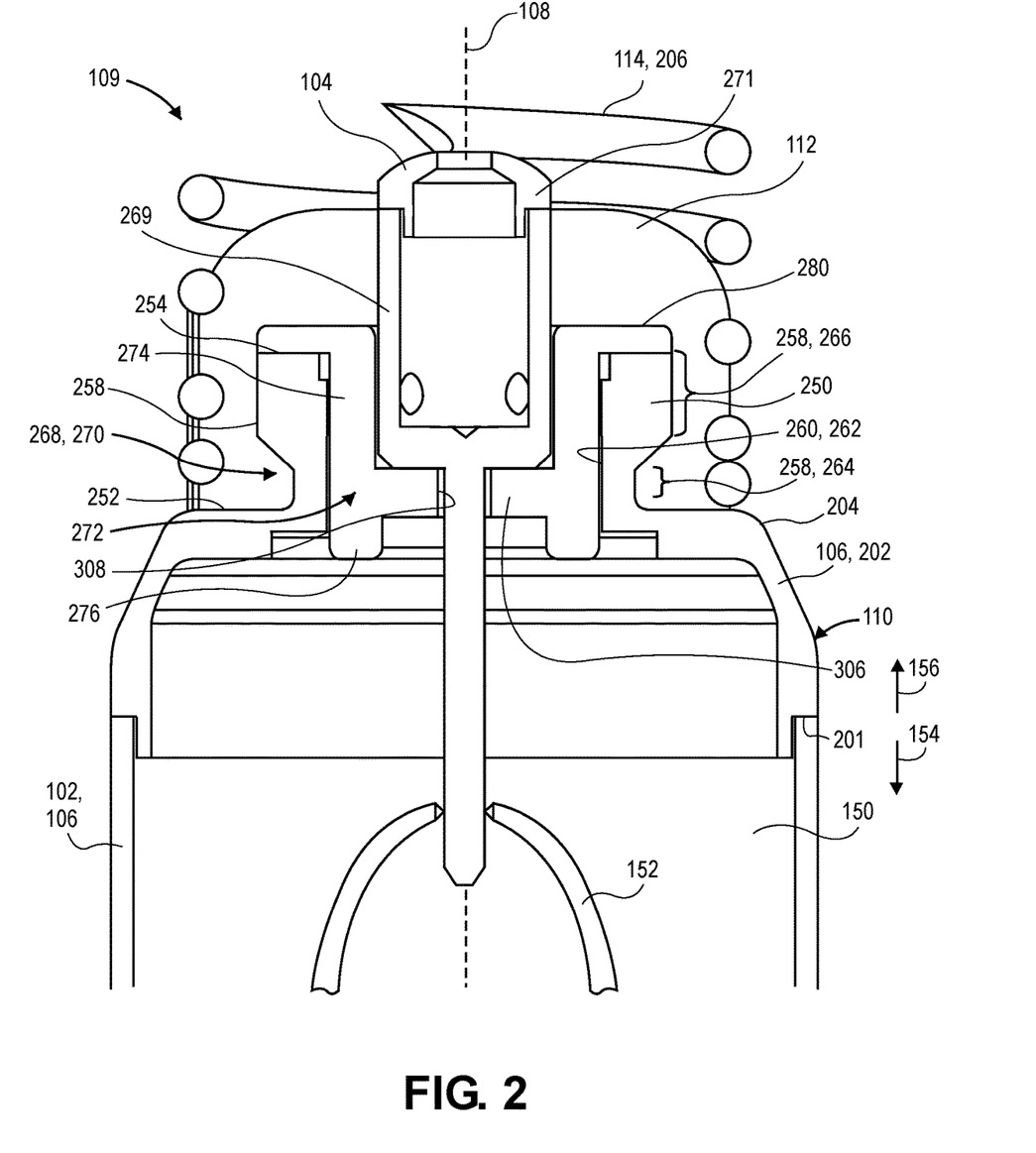
FIG. 2 is a sectional view of a header assembly mounted on a housing of a leadless biostimulator, in accordance with an embodiment.

Referring to FIG. 2, a sectional view of a header assembly mounted on a housing of a leadless biostimulator is shown in accordance with an embodiment. The electrical feedthrough assembly 110 of the header assembly 109 can include a flange 202. The flange 202 can have a proximal lip 201 to mount on the housing wall surrounding the electronics compartment 150. In one implementation, the flange 202 is formed from titanium. The flange 202 can be mounted on the housing 102 and connected to the housing by a hermetic seal, e.g., a weld or any other similar hermetically sealed connection. For example, the hermetic weld can be formed circumferentially around a seam between a proximal end of the flange 202, e.g., the proximal lip 201, and a distal end of the housing 102.

In an embodiment, the flange 202 includes a shoulder 204 and a mounting wall 250 extending distally along the longitudinal axis 108. The shoulder 204 can be a transition region between a flange wall that extends substantially longitudinally from the proximal lip 201 to a flange wall that extends substantially transversely. The mounting wall 250 can receive the helix mount 112.

In one implementation, the fixation element 114 includes a helix 206 mounted on the helix mount 112. The helix 206 can extend distally from the helix mount 112 about the longitudinal axis 108. For example, the helix 206 can revolve about the longitudinal axis 108. The helix 206 can include a spiral wire, formed by coiling or cut from a wall of a length of tubing, which extends in a rotational direction around the longitudinal axis 108. For example, the helix 206 can revolve in a right-handed direction about the longitudinal axis 108. The helix 206 can be suitable for attaching the biostimulator 100 to tissue, such as heart tissue. For example, in the case of a right-handed spiral direction, the biostimulator 100 can be advanced into contact with a target tissue, and the biostimulator 100 can then be rotated in the right-handed direction to screw the helix 206 into the tissue. Torque can be transmitted from the housing 102 to the helix 206 through the electrical feedthrough assembly 110 and helix mount 112, and thus, mechanical stability of the header assembly components facilitates torque transmission. In an embodiment, the helix mount 112 can be overmolded on the flange 202, as described below, to provide mechanical stability.

The biostimulator 100 can be implanted in a body region having fluids, e.g., within the blood of a heart chamber, and thus, portions of the biostimulator 100 can be sealed and/or protected against fluid ingress that may compromise functionality of the biostimulator 100. For example, portions of the electrical feedthrough assembly 110, such as the flange 202, may be coated with a protective coating to prevent short circuiting of the distal electrode 104 and the proximal electrode 106.

In one implementation, the distal electrode 104 is spatially near the flange 202, which can be a portion of the proximal electrode 106. Thus, if blood were allowed to fill the gap between the distal electrode 104 and the flange 202, the electrodes could be electrically shorted and pacing impulses may not properly pace the cardiac tissue. Accordingly, a barrier can be included in the biostimulator 100 to prevent blood from filling a cavity within the biostimulator 100 between the distal electrode 104 and the proximal electrode 106. In an embodiment, the barrier includes the overmolded helix mount 112 that separates the flange 202 and the electrode 104, and that conforms and adheres to an insulator 276 between the flange 202 and the electrode 104 to electrically isolate the components.

The electrical feedthrough assembly 110 can be a multifunction component. For example, unlike a traditional pacemaker where the electrical feedthrough is separated from the pacing site by a lead, the distal electrode 104 of the electrical feedthrough assembly 110 of the biostimulator 100 may be in direct contact with the stimulation site. Accordingly, the electrical feedthrough assembly 110 can not only serve as the electrical pass-through from a hermetic package to a surrounding environment, but may also serve other functions, such as providing a housing for a steroid or other filler (not shown) and directing tissue interaction. Additionally, the electrical feedthrough assembly 110 can be a filtered or unfiltered assembly. More particularly, the electrical feedthrough assembly 110 can incorporate an integral EMI filter capacitor (filtered feedthrough assembly) or not (unfiltered feedthrough assembly). These and other embodiments of the electrical feedthrough assembly 110 have been described in U.S. patent application Ser. No. 16/662,282, filed on Oct. 24, 2019, titled "BIOSTIMULATOR FEEDTHROUGH HAVING INTEGRATED ELECTRODE CUP," the contents of which are incorporated herein by reference in their entirety. In the interest of brevity, the details of such embodiments are not repeated in detail here.

In an embodiment, the flange 202 includes the mounting wall 250 to receive the helix mount 112. The shoulder 204 of the flange 202 can have a distal shoulder surface 252 extending transverse to the longitudinal axis 108, and the mounting wall 250 can extend from the distal shoulder surface 252 along the longitudinal axis 108. For example, the mounting wall 250 can extend in the distal direction 156 from a proximal wall end at the distal shoulder surface 252 to a distal wall end 254 at a distalmost location. The mounting wall 250 can extend around and/or surround the longitudinal axis 108 between the distal wall end 254 of the shoulder 204 and the distal wall end 254. For example, one or more portions of the mounting wall 250 can be annular wall portions that encircle the longitudinal axis 108. Accordingly, the mounting wall 250 can include an outer surface 258 facing radially outward from the longitudinal axis 108 and an interior surface 260 facing radially inward toward the longitudinal axis 108. The interior surface 260 can define a central channel 262 extending through the mounting wall 250 to provide a passage between a proximal side and a distal side of the electrical feedthrough assembly 110.

In an embodiment, the outer surface 258 of the mounting wall 250 is threadless. Rather than having threads, the mounting wall 250 can incorporate one or more undercuts or collars, as described below. The undercuts or collars can act as mechanical reinforcements to ensure that the overmolded helix mount 112 attaches and/or adheres to the flange 202. For example, the outer surface 258 may have one or more smooth and/or textured surfaces without having a helical rib used to connect the mounting wall 250 to another component, such as the helix mount 112. It will be appreciated that the threadless outer surface 258 may not be ridgeless. For example, the outer surface 258 may include one or more circumferential ridges. The outer surface 258 can also incorporate other textures, such as a knurled surface or one or more prongs extending radially outward.

As shown in FIG. 2, the threadless outer surface 258 may extend along several portions of the mounting wall 250, longitudinally between the distal shoulder surface 252 and the distal wall end 254. A proximal portion of the mounting wall 250 can be a neck 264. The neck 264 can extend distally from the distal shoulder surface 252 toward a distal portion of the mounting wall 250, e.g., a collar 266. As shown, a transition portion may be located between the neck 264 and the collar 266. For example, the transition portion can be a frustoconical surface flaring radially outward in a distal direction 156 from a distal end of the neck 264 to a proximal end of the collar 266.

In an embodiment, the outer surface 258 of the mounting wall 250 includes a recess 268. The recess 268 can be an indentation or another volumetric feature defined by a portion of the outer surface 258 that is radially inward from an outermost point of the surface. The recess 268 can extend around the longitudinal axis 108, partly or wholly. For example, the recess 268 can be an arc-shaped groove that extends partly around the longitudinal axis 108. Several such grooves can be distributed around the mounting wall 250 to provide several grip points for the helix mount 112.

The recess 268 may extend entirely around the longitudinal axis 108. For example, the recess 268 can be defined by the collar 266, the neck 264, and the distal shoulder surface 252. The neck 264 includes a portion of the outer surface 258 that is radially inward (nearer to the longitudinal axis 108) than the portion of the outer surface 258 on the collar 266 or the distal shoulder surface 252. Thus, the recess 268 can extend around the neck 264. In the case of the collar 266, neck 264, and shoulder 204 having cylindrical surfaces revolved about the longitudinal axis 108, the recess 268 can be a circumferential groove 270 around the neck 264.

The recess 268 may be longitudinally disposed between the distal shoulder surface 252 and the collar 266. More particularly, a reference axis extending parallel to the longitudinal axis 108 and passing through the recess 268 intersects a distal surface of the shoulder 204 and a proximal surface of the collar 266 (or the transition region between the neck 264 and the collar 266). Accordingly, when the collar 266 and neck 264 are cylindrical, the recess 268 can be the circumferential groove 270 longitudinally between the collar 266 and the distal shoulder surface 252.

Additional details of the flange 202 and the mounting wall features are provided below, e.g., with respect to FIGS. 5-6. At this point, however, it will be appreciated that the electrical feedthrough assembly 110 can include a recess 268 that provides a volume to receive a portion of an overmolded helix mount 112. The helix mount material that flows into the recess 268 can provide adhesion and interference with the surrounding recess surface to resist removal of the helix mount 112 from the flange 202. Prior to describing the overmolded helix mount 112 in additional detail, several other components of the electrical feedthrough assembly 110 shall be introduced.

In certain implementations, each of the components of the electrical feedthrough assembly 110 may be symmetrically formed about the longitudinal axis 108. For example, the cross-sectional area of the electrode body illustrated in FIG. 2 can be swept about the longitudinal axis 108 such that the pin and the cup have cylindrical profiles. In other implementations, the profiles of the components of the electrical feedthrough assembly 110 may be non-cylindrical. For example, a cross-section of the electrode body taken about a transverse plane extending orthogonal to the longitudinal axis 108 may reveal an outer surface of the pin and/or the cup that is square, pentagonal, elliptical, etc., or any other suitable shape. Accordingly, the particular shapes illustrated in the figures are provided by way of example only and not necessarily by way of limitation.

In an embodiment, the distal electrode 104 may include an electrode body 269 and/or an electrode tip 271. In implementations of the present disclosure, the electrode tip 271 may be mounted on the electrode body 269, e.g., on a distal end of the electrode body, as illustrated in FIG. 2. The distal electrode 104 can be disposed within the central channel 262 of the mounting wall 250. The distal electrode 104 can be isolated, however, from a ground component. More particularly, the distal electrode 104 can be separated from the flange 202 by the insulator 272.

Feedthrough assemblies in accordance with the present disclosure may include a monolithic electrode body. For example, the monolithic electrode body can have several distinct portions that are integrally formed with each other. In one implementation, the electrode body 269 includes a cup and a pin that are integrally formed such that the electrode body is monolithic, or, in other words, has a unitary or single-piece construction. More particularly, the cup and the pin can be formed from a single blank of material, as described below, to produce the electrode body 269 such that the electrode body does not have any seams, welds, etc. As illustrated in FIG. 2, the pin can be sized to fit through an insulator hole 308 of the insulator 272, and the cup can be sized to fit within the distal cavity of the insulator 272. Accordingly, the monolithic electrode body provides an electrical pathway from the electronics compartment 150, which is proximal to an insulator base 306, to the cup distal to the insulator base 306.

The cup and the pin can serve as the electrically active path from the electronics assembly 152 within the electronics compartment 150 to the patient-contacting pacing electrode tip. The integrally formed cup and pin can be of the same material. For example, and without limitation, the electrode body can be formed from 90/10 platinum/iridium alloy or another suitable conductive alloy.

The biostimulator 100, and more particularly the electrical feedthrough assembly 110, can include a filler (not shown), such as a monolithic controlled release device (MCRD). The filler may include a therapeutic material, and can be loaded into the cup of the electrode body 269. Accordingly, the filler can deliver a specified dose of a therapeutic agent, e.g., a corticosteroid, into target tissue at an implantation site of the biostimulator 100 within a patient. In at least one implementation, the therapeutic agent can include a corticosteroid, such as dexamethasone sodium phosphate, dexamethasone acetate, etc.

When the biostimulator 100 is implanted at the target site, blood can flow into the electrode cavity through a hole in the electrode tip 271 and cause the filler to elute the therapeutic agent. Elution of the filler can be controlled by its own geometry, as well as by a size of the electrode cavity and the geometry of the electrode body. Accordingly, the therapeutic agent can flow, or weep, from the MCRD through the tip hole to the target tissue. When the therapeutic agent is consistently released into the target tissue, the controlled dose can reduce inflammation associated with the device implantation. Furthermore, the electrode tip 271 can be conductive, and electrically in contact with the electrode body, such that pacing impulses transmitted through the electrode body 269 from the electronics assembly 152 can travel through the electrode tip 271 to the target tissue.

The insulator 272 of the electrical feedthrough assembly 110 may include an insulator wall 274 surrounding a portion of the electrode body. More particularly, the insulator wall 274 can extend from a proximal insulator end 276 to a distal insulator end 280, and over the length, the insulator wall 274 can be disposed between the electrode 104 and the mounting wall 250. Thus, the insulator 272 can contain and separate the conductive electrode body 269, which is conductive, from the mounting wall 250 of the flange 202, which may also be conductive. The insulator 272 can be formed from a ceramic, e.g., alumina, ruby, glass, or another insulating material. Accordingly, the insulator 272 can electrically insulate the distal electrode 104 from the flange 202. The insulator 272 can be brazed to the flange 202. For example, a brazed joint may be formed between the interior surface 260 of the mounting wall 250 and an outer surface of the insulator 272.

Figure 3:
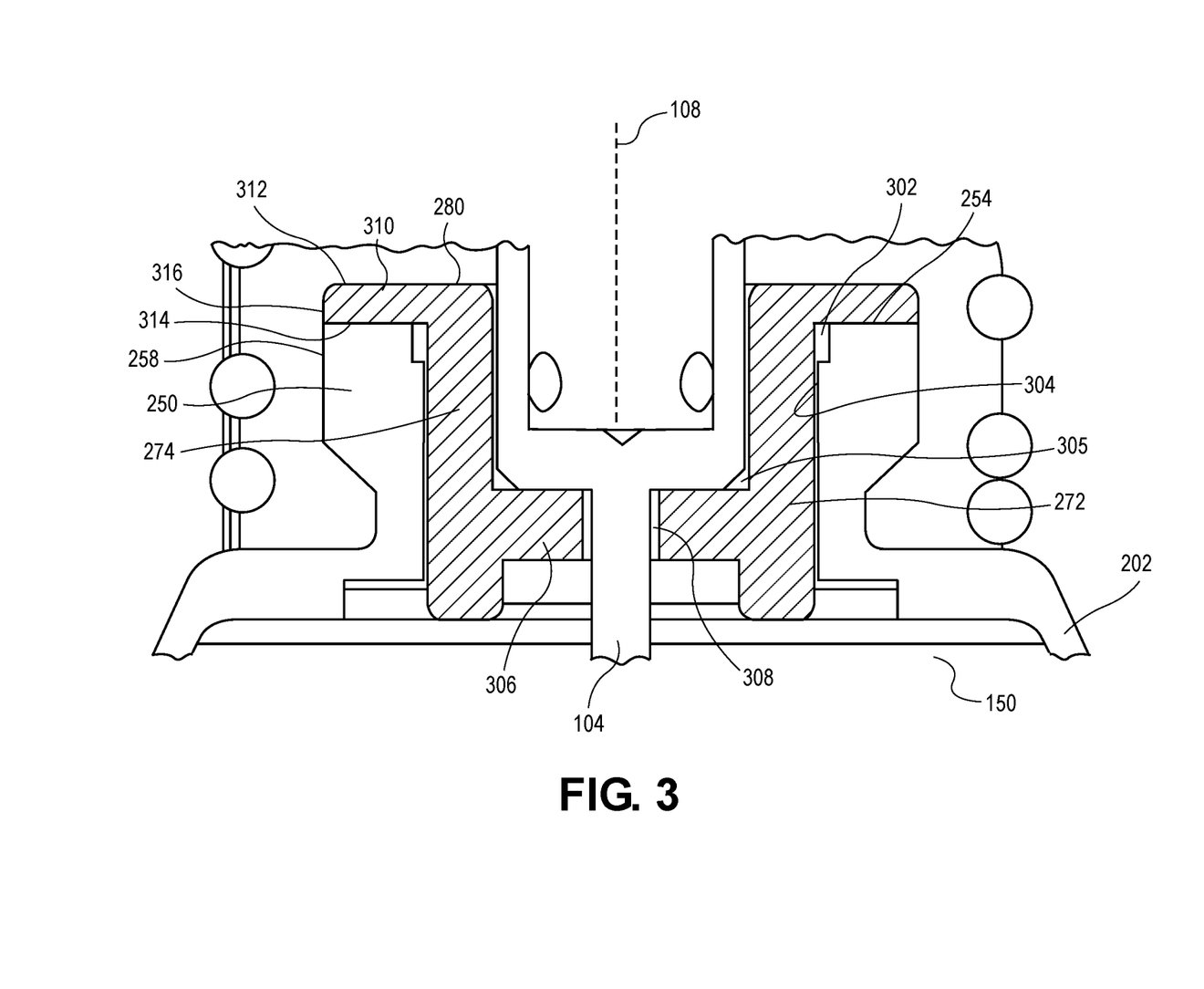
FIG. 3 is a sectional view of an insulator within a flange of a header assembly for a leadless biostimulator, in accordance with an embodiment.

Referring to FIG. 3, a sectional view of an insulator within a flange of a header assembly for a leadless biostimulator is shown in accordance with an embodiment. In one implementation, the flange 202 includes a mounting hole 302 that, when the biostimulator 100 is assembled, extends distally from the electronics compartment 150 on a proximal side of the mounting wall 250 along the longitudinal axis 108 and through the distal wall end 254 to a surrounding environment. More particularly, the mounting hole 302 provides a channel between the electronics compartment 150 and the surrounding environment. The mounting wall 250 of the flange 202 can extend around the mounting hole 302. For example, an inner surface 304 of the mounting wall 250 can define the mounting hole 302.

In one implementation, the insulator 272 has an insulator wall 274 extending distally from an insulator base 306. In one implementation, the insulator wall 274 can be cylindrical, having an outer diameter and an inner diameter; however, other insulator shapes may be used in other implementations of the present disclosure. The outer diameter of the insulator wall 274 can be sized to fit within the mounting hole 302 of the flange 202. Similarly, an interior of the insulator wall 274 can define an insulator channel 305 sized to receive the electrode 104.

In certain implementations, the insulator base 306 can be a lateral wall extending across the interior of the insulator 272 orthogonal to the longitudinal axis 108. More particularly, the insulator base 306 can be a transverse wall separating a distal cavity of the insulator 272 from a proximal cavity of the insulator 272, with the cavities being radially inward from the insulator wall 274. In one implementation, an insulator hole 308 extends through the insulator base 306 along the longitudinal axis 108. Accordingly, when the insulator 272 is mounted within the mounting hole 302 of the flange 202, the insulator hole 308 provides a channel between the electronics compartment 150 and the surrounding environment.

In implementations of the present disclosure, the insulator 272 may include one or more insulator holes 308, each providing a feedthrough channel. The feedthrough channels can receive corresponding pins (such as a pin of the electrode 104 extending along the longitudinal axis 108). Accordingly, the electrical feedthrough assembly 110 can allow multi-faceted pacing or sensing feedthroughs to increase device capability. For example, the feedthrough pins can provide multi-site pacing, helix strain measurement, etc. A multi-polar feedthrough can provide activation of several components of the biostimulator 100, facilitating alternate pacing, sensing, or communication options. The increased capability may also be facilitated by providing several power and/or data feeds into the electronics compartment 150.

The insulator 272 can include a sealing collar 310 extending radially outward from the insulator wall 274 at the distal insulator end 280. The sealing collar 310 provides a ledge radially outward from the insulator wall 274. The ledge can include a top surface 312 facing in the distal direction 156 and a bottom surface 314 facing in the proximal direction 154. The radial ledge provided by the sealing collar 310 can create an extended electrical path between the electrode 104 and the flange 202. Increasing a distance of the electrical path between the electrode 104 and the flange 202 can electrically isolate those components to reduce a risk of short-circuiting between the distal electrode 104 and the proximal electrode 106.

The sealing collar 310 can also provide additional sealing surface area between the insulator 272 and the mounting wall 250. In an embodiment, the sealing collar 310 at least partly covers the distal wall end 254 of the mounting wall 250. For example, the bottom surface 314 of the sealing collar 310 can face and extend over a surface of the distal wall end 254. The facing surfaces can inhibit fluid flow from within the mounting hole 302 to an area radially outward from the mounting wall 250.

The sealing collar 310 may have an outer collar surface 316. The outer collar surface 316 can have an outer dimension measured transverse to the longitudinal axis 108. In an embodiment, as shown in FIG. 3, the outer collar dimension may be the same as an outer dimension of the mounting wall 250. More particularly, the outer collar surface 316 and the outer surface 258 of the mounting wall 250 can be at the same radial location relative to the longitudinal axis 108.

Figure 4:
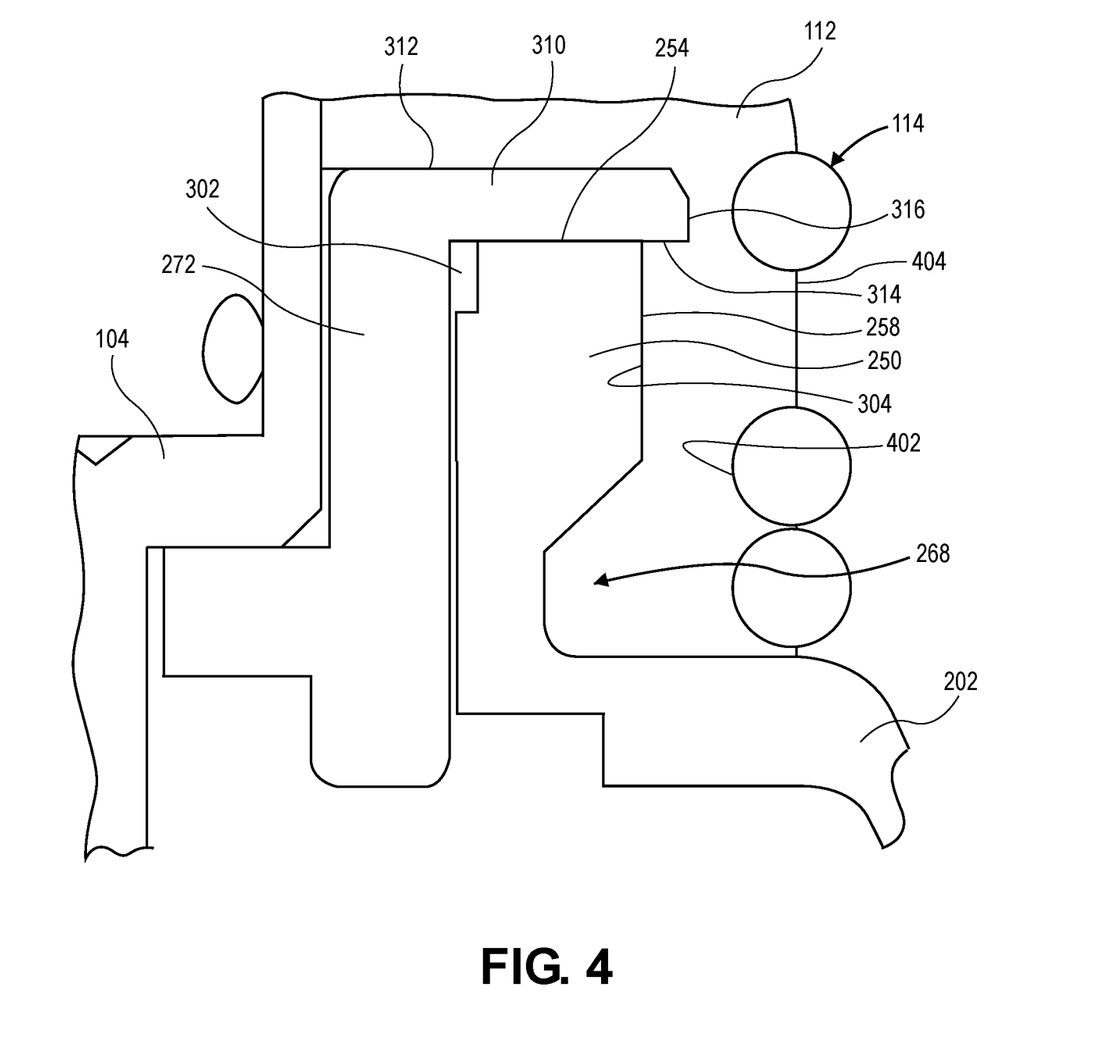
FIG. 4 is a sectional detail view of an insulator within a flange of a header assembly for a leadless biostimulator, in accordance with an embodiment.

Referring to FIG. 4, a sectional detail view of an insulator within a flange of a header assembly for a leadless biostimulator is shown in accordance with an embodiment. In an embodiment, the sealing collar 310 is wider than the mounting wall 250. For example, the outer collar surface 316 may be at a location that is radially outward from an outermost point on the distal wall end 254. More particularly, the outer collar surface 316 may be radially outward from the outer surface 258 of the mounting wall 250. Such an overhang of the sealing collar 310, caused by the outer diameter of the insulator overhang being larger than the outer diameter of the flange 202, may further enhance electrical isolation between the electrode 104 and the flange 202. The ledge increases the electrical pathway between the electrode 104 and the flange 202, which contributes to such electrical isolation.

Furthermore, protrusion of the sealing collar 310 outward from the mounting wall 250 can provide a lip to engage the helix mount 112 for mechanical reinforcement between the helix mount 112 and the electrical feedthrough assembly 110. For example, as described above, the helix mount 112 can conform to the top surface 312 of the sealing collar 310, and thus, the increased surface area provided by the ledge can facilitate adhesion between the helix mount 112 and the insulator 272. Similarly, when the sealing collar 310 is wider than the distal wall end 254 and the helix mount 112 is overmolded around the insulator 272, the helix mount 112 can conform to the bottom surface 314 of the sealing collar 310. The overmolded helix mount 112 can therefore grip the lip of the sealing collar 310 to retain the helix mount 112 on the electrical feedthrough assembly 110. The insulator 272 protrudes outward from the flange 202 and acts as another mechanical reinforcement to prove adhesion and mechanical resistance to removal of the molded plastic of the helix mount 112 from the flange 202.

Still referring to FIG. 4, the helix mount 112 can be overmolded on the flange 202 such that the helix mount 112 fills the recess 268 of the mounting wall 250. The overmolding process allows the helix mount 112 to be formed from a polymer that is flowed around or into one or more collars or undercuts, and thus, the overmolded material can conform closely to the flange 202 and the insulator 272. In an embodiment, the overmolded helix mount 112 is in intimate contact along the entire outer surface of the mounting wall 250 and the top, bottom, and outer surfaces of the sealing collar 310. Accordingly, the inner surface 304 of the helix mount 112 can adhere to the outer surface 258 of the mounting wall 250, as well as the surfaces of the insulator 272.

Advantageously, overmolding the helix mount 112 on the flange 202 may avoid certain limitations of machining processes. For example, rather than cutting threads into the helix mount 112, the helix mount 112 can be directly formed on and around the mounting wall 250. Injection molding of the helix mount 112 can allow for maximized adhesive efficiency that no longer requires additional sealing components and materials. For example, sealing gaskets, medical adhesives, and other components that may be required for a threaded flange-to-helix mount assembly may be eliminated by overmolding the components directly on each other. This can result in a cost-effective device having few parts that are mechanically stable.

The overmolding process may incorporate other components of the biostimulator 100. For example, the fixation element 114 may be at least partly embedded within the helix mount 112. Embedding the fixation element 114 can occur during a same overmolding process used to mold the helix mount 112 on the flange 202. An inner diameter 402 of the fixation element 114 may be radially inward of an outer mount surface 404 of the helix mount 112. Thus, the embedded fixation element 114 can be secured by the overmolded helix mount 112 to resist movement or removal from the device. The embedded fixation element 114 can be mechanically robust and reduce a likelihood of the fixation element 114 dislodging within a patient.

Figure 5:
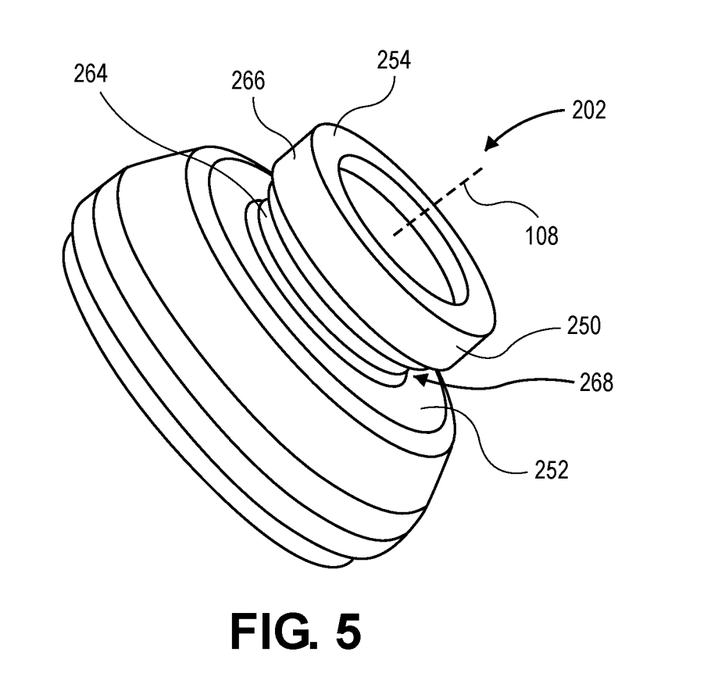
FIG. 5 is a perspective view of a flange of a header assembly, in accordance with an embodiment.

Referring to FIG. 5, a perspective view of a flange of a header assembly is shown in accordance with an embodiment. The flange 202 can be machined or molded to include the features described above. For example, the flange 202 may be symmetrically formed about the longitudinal axis 108 such that the mounting wall 250 extends distally from the distal shoulder surface 252. The mounting wall 250 includes one or more collars 266 or undercuts to create recesses 268 in relief. The recesses 268 receive overmolded helix mount material to join the helix mount 112 to the flange 202. It will be appreciated that the term "undercut" does not imply that the recesses 268 are formed by a mechanical cutting process, although the undercuts may be. More particularly, the flange 202 may be molded from a polymer, and thus, the undercuts may result from a mold contour.

Figure 6:
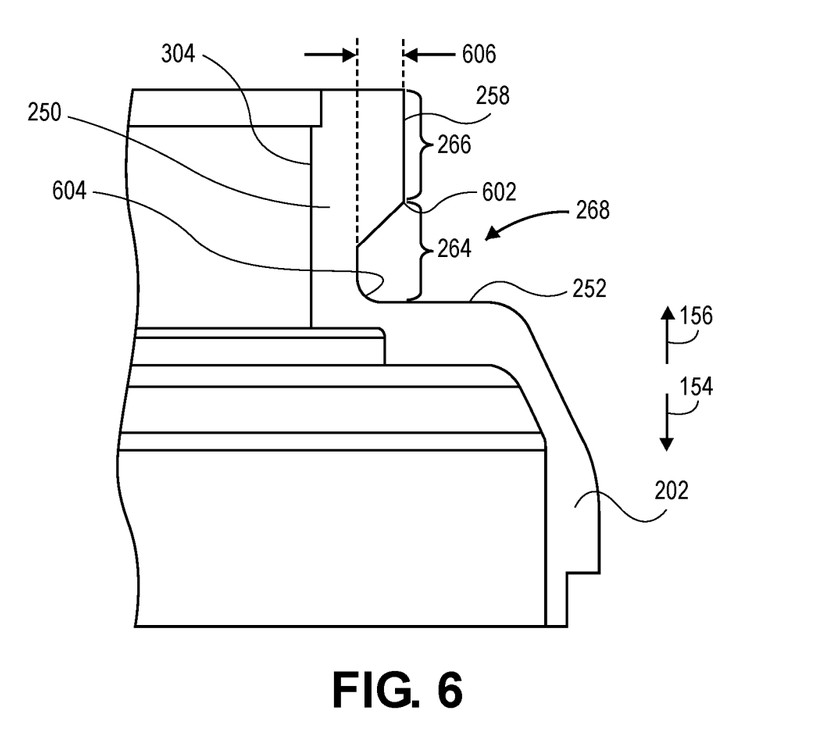
FIG. 6 is a sectional view of a flange of a header assembly, in accordance with an embodiment.

Referring to FIG. 6, a sectional view of a flange of a header assembly is shown in accordance with an embodiment. An undercut, or recess 268, of the mounting wall 250 can be defined between the distal shoulder surface 252 and the collar 266 of the flange 202. In an embodiment, the recess 268 includes a distal recess edge 602 and a proximal recess edge 604 separated longitudinally along the outer surface 258 of the mounting wall 250. A contour of the outer surface 258 of the mounting wall 250 may have a radial distance from the longitudinal axis 108 that varies between the distal recess edge 602 and proximal recess edge 604. More particularly, a depth 606 of the recess 268 may vary between the distal recess edge 602 and the proximal recess edge 604.

In an embodiment, the depth 606 increases in the proximal direction 154 from the collar 266 toward the distal shoulder surface 252. For example, the distal recess edge 602 may have a larger radial dimension than the proximal recess edge 604, and the contour of the mounting wall 250 may trend inward in a stepped manner, continuously, or over any other contour path.

The contour of the mounting wall 250 may trend inward in a stepped manner. As shown in FIG. 6, the outer surface 258 may taper inwardly from the distal recess edge 602 to the depth 606 at a proximal end of the intermediate section of the mounting wall 250. The outer surface 258 may then maintain a same width at the depth 606 from the intermediate section to the distal shoulder surface 252 (or a fillet or chamfer that transitions into the distal shoulder surface 252 at proximal recess edge 604).

The contour of the mounting wall 250 may trend inward continuously. For example, the outer surface 258 may taper inwardly from the distal recess edge 602 to the proximal recess edge 604 over a constant slope. Thus, rather than having an intermediate and proximal section of the neck 264, the neck 264 may be a continuously tapering section of the mounting wall 250. It will be appreciated that the stepped or continuous taper of the recess 268 may also taper inwardly in the distal direction 156. For example, the outer surface 258 of the mounting wall 250 may reduce abruptly from the distal recess edge 602 to the depth 606, and then increase in width gradually toward the distal shoulder surface 252. In other words, the skilled artisan would understand that the recess 268 may have any contour that provides an indentation or negative space within the mounting wall 250 that allows the helix mount material to flow into the recess 268 and adhere to the mounting wall 250 surface.

Adhesion between the helix mount 112 and the flange 202, and resistance to removal of the helix mount 112, may be facilitated by the depth 606 of the recess 268. More particularly, a deeper recess 268 may better hold the helix mount 112 because the deeper undercut can allow for a strong grip between the helix mount 112 and the flange 202. For example, the depth 606 of the recess 268 may be at least 5% of a width of the collar 266 and/or at least 50% of a thickness of the collar 266 between the outer surface 258 and the inner surface 304 of the mounting wall 250. Such ranges are provided by way of example.

Figure 7:
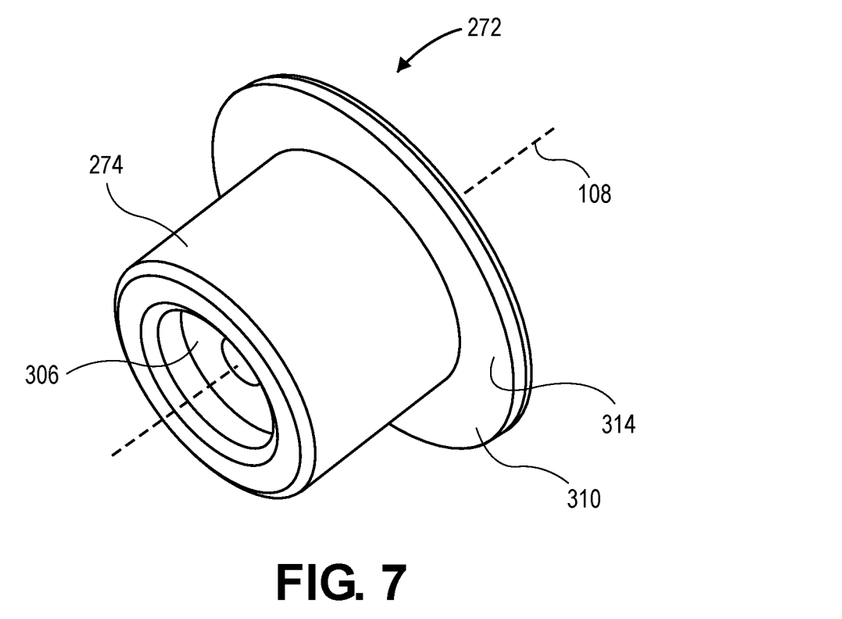
FIG. 7 is a perspective view of an insulator of a header assembly, in accordance with an embodiment.

Referring to FIG. 7, a perspective view of an insulator of a header assembly is shown in accordance with an embodiment. Like the flange 202, the insulator 272 may be symmetrically formed about a longitudinal axis 108. For example, the insulator wall 274 can be an annular wall extending along the longitudinal axis 108, and the insulator base 306 can be an annular disc extending transverse to the longitudinal axis 108. The sealing collar 310 may also be an annular disc-shaped wall that extends radially outward from the insulator wall 274 to form the ledge. As described below, the insulator 272, the flange 202, the electrode 104, the helix mount 112, and the fixation element 114, may be assembled to form the header assembly 109.

Figure 8:
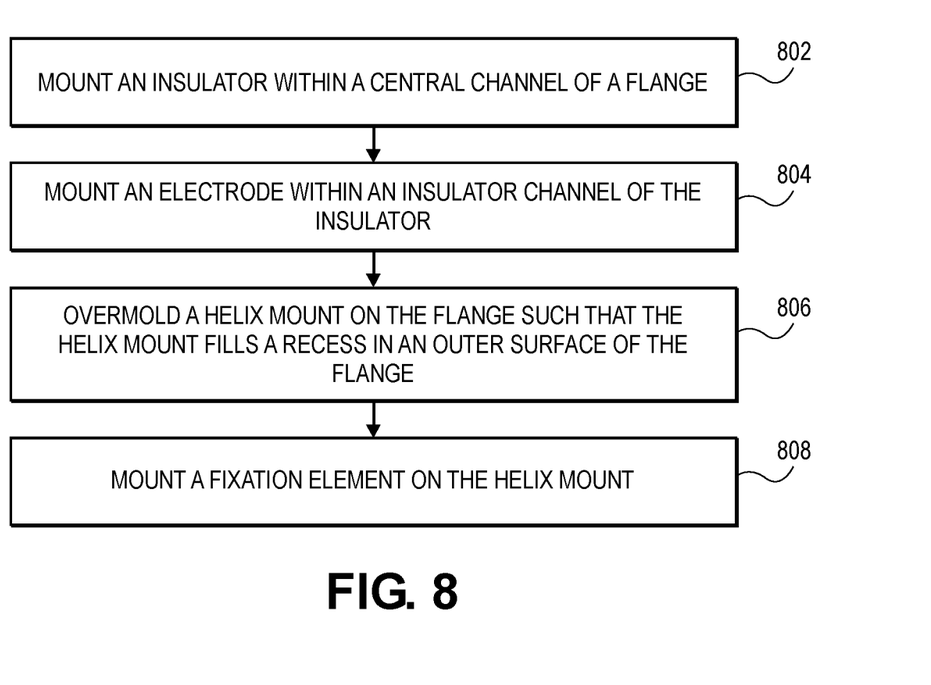
FIG. 8 is a flowchart of a method of manufacturing a header assembly for a leadless biostimulator, in accordance with an embodiment.

Referring to FIG. 8, a flowchart of a method of manufacturing a header assembly for a leadless biostimulator is shown in accordance with an embodiment. Based on the assembled structure described above, it can be appreciated that the individual components of the electrical feedthrough assembly 110, and the header assembly 109 as a whole, can be fit together during assembly, e.g., during a method of manufacturing. For example, at operation 802, the insulator 272 may be mounted within the central channel 262 of the flange 202. The annular insulator wall 274 can be inserted into the central channel 262 and advanced until the bottom surface 314 of the sealing collar 310 directly contacts the distal wall end 254.

At operation 804, the electrode 104 is mounted within the insulator channel 305 of the insulator 272. The pin of the electrode body 269 can be inserted through the insulator hole 308 of the insulator base 306. When the pin is installed in the insulator hole 308, the electrode 104 can be advanced until a proximal face of the electrode cup faces and/or directly contacts a distal face of the insulator base 306.

In a subsequent example operation, the electrode body can be bonded to the insulator 272. The bond between the electrode body and the insulator 272 can provide a mechanical attachment between the components, as well as a seal between the electrode pin and the insulator base 306 to prevent ingress or egress of fluids or energy source chemicals through portions of the insulator hole 308 that is not plugged by the electrode pin. Thus, the bond between the components can be a hermetic seal. For example, the electrode pin can be bonded to the insulator 272 by a braze joint. The braze joint can include, but is not limited to, gold brazing that flows at least partially into the insulator hole 308 to secure and seal the pin.

In another subsequent example operation, the insulator 272 can be bonded to the flange 202. The bond between the insulator 272 and the flange 202 can provide a mechanical attachment between the components, as well as a seal between the insulator wall 274 and the mounting wall 250 to prevent ingress or egress of fluids or energy source chemicals through a portion of the mounting hole 302 that is not plugged by the insulator 272. Accordingly, the bond between the components can be a hermetic seal. For example, and without limitation, the insulator 272 can be bonded to the flange 202 by a second braze joint. The second braze joint can include gold brazing that flows at least partly into the mounting hole 302 to secure and seal the insulator 272.

In other example operations, the filler can be inserted into the electrode cavity and/or the electrode tip 271 can be mounted on a distal end of the electrode cup. For example, the electrode tip 271 can be placed in contact with the distal end of the electrode body 269 around a circumference of the distal end. The electrode tip 271 can then be joined to the electrode body 269 by a circumferential bond. For example, an adhesive or thermal weld may be formed between the distal end of the cup and the electrode tip 271.

The helix mount 112 can be formed directly on the electrical feedthrough assembly 110. At operation 806, the helix mount 112 is overmolded on the flange 202 such that the helix mount material fills the recess 268 and covers the outer surface 258 of the flange 202. As the helix mount 112 is molded onto the flange 202, the inner surface 304 of the helix mount 112 spreads over the outer surface 258 of the mounting wall 250. For example, an adhesion path can extend over the distal shoulder end 252, the neck 264, the collar 266, and/or distal wall end 254, providing an extended adhesion pathway such that the helix mount 112 adheres to and grips the surface of the flange 202.

At operation 808, the fixation element 114 is mounted on the helix mount 112. The fixation element 114 may be embedded within the helix mount 112 as described above. The fixation element 114 may, however, be mounted on the helix mount 112 in other manners. For example, a holding thread may be molded or machined into an external surface of the helix mount 112 to receive the fixation element 114.

The assembled header assembly 109 may be mounted on the housing 102 of the biostimulator 100. The electrical feedthrough assembly 110 can connect to electronics assembly 152 to transmit sensing and/or pacing pulses from the electronics compartment 150 to target tissue. Furthermore, fixation element 114 can hold the electrical feedthrough assembly 110 in close contact to the target tissue via the helix mount 112. Given the overmolded helix mount structure described above, the attachment between the fixation element 114 and the electrical feedthrough assembly 110 can be robust, and thus, pacing of the target tissue can be reliable.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A header assembly for a leadless biostimulator, comprising:
   a flange including a mounting wall having a central channel extending along a longitudinal axis, wherein the mounting wall includes a neck and a collar, wherein the neck has a neck surface extending longitudinally from a distal shoulder surface of a shoulder to the collar, wherein the collar has a collar surface radially outward from the neck surface, and wherein an outer surface of the mounting wall defines a recess extending around the longitudinal axis and the neck;
   a helix mount overmolded on the flange such that the helix mount entirely fills the recess and covers the neck within the recess longitudinally between the distal shoulder surface and the collar, wherein the helix mount includes a hole aligned with the central channel of the mounting wall;

a fixation helix mounted on the helix mount; and an electrode disposed within the central channel of the mounting wall and exposed to a surrounding environment through the hole.

2. The header assembly of claim 1, wherein an inner surface of the helix mount adheres to the outer surface of the mounting wall.

3. The header assembly of claim 1, wherein the outer surface is threadless.

4. The header assembly of claim 1, wherein the collar, the neck, and the distal shoulder surface define the recess as a circumferential groove around the neck.

5. The header assembly of claim 4, wherein the circumferential groove is longitudinally between the collar and the distal shoulder surface.

6. The header assembly of claim 1, wherein a depth of the recess increases in a proximal direction from the collar toward the distal shoulder surface.

7. The header assembly of claim 1 further comprising an insulator including an insulator wall extending from a proximal insulator end to a distal insulator end between the electrode and the mounting wall, and a sealing collar extending radially outward from the insulator wall at the distal insulator end.

8. The header assembly of claim 7, wherein the sealing collar at least partly covers a distal wall end of the mounting wall, and wherein the helix mount conforms to a distal surface of the sealing collar.

9. The header assembly of claim 8, wherein the sealing collar is wider than the distal wall end, and wherein the helix mount conforms to a proximal surface of the sealing collar.

10. The header assembly of claim 1, wherein the fixation helix includes a helix revolving about the longitudinal axis.

11. The header assembly of claim 1, wherein the fixation helix is at least partly embedded within the helix mount.

12. A leadless biostimulator, comprising:

a housing having a longitudinal axis and an electronics compartment;

an electronics assembly mounted in the electronics compartment; and a header assembly mounted on the housing, wherein the header assembly includes a flange including a mounting wall having a central channel extending along the longitudinal axis, wherein the mounting wall includes a neck and a collar, wherein the neck has a neck surface extending longitudinally from a distal shoulder surface of a shoulder to the collar, wherein the collar has a collar surface radially outward from the neck surface, and wherein an outer surface of the mounting wall defines a recess extending around the longitudinal axis and the neck, a helix mount overmolded on the flange such that the helix mount entirely fills the recess and covers the neck within the recess longitudinally between the distal shoulder surface and the collar, wherein the helix mount includes a hole aligned with the central channel of the mounting wall, a fixation helix mounted on the helix mount, and an electrode disposed within the central channel of the mounting wall and exposed to a surrounding environment through the hole.

13. The leadless biostimulator of claim 12, wherein an inner surface of the helix mount adheres to the outer surface of the mounting wall.

14. The leadless biostimulator of claim 12, wherein the collar, the neck, and the distal shoulder surface define the recess as a circumferential groove around the neck.

15. The leadless biostimulator of claim 12, wherein the header assembly includes an insulator including an insulator wall extending from a proximal insulator end to a distal insulator end between the electrode and the mounting wall, and a sealing collar extending radially outward from the insulator wall at the distal insulator end.

16. The leadless biostimulator of claim 12, wherein the fixation helix includes a helix revolving about the longitudinal axis.

17. A method, comprising:

mounting an insulator within a central channel of a flange of a leadless biostimulator, wherein the flange has a longitudinal axis and includes a mounting wall including a neck and a collar, wherein the neck includes a neck surface extending from a distal shoulder surface of a shoulder to the collar, wherein the collar has a collar surface radially outward from the neck surface, and wherein an outer surface of the mounting wall defines a recess extending around the longitudinal axis and the neck;

overmolding a helix mount on the flange such that the helix mount entirely fills the recess and covers the neck within the recess longitudinally between the distal shoulder surface and the collar; and mounting a fixation helix on the helix mount.

18. The method of claim 17, wherein the collar, the neck, and the distal shoulder surface define the recess as a circumferential groove around the neck.

19. The method of claim 17, wherein the insulator includes an insulator wall extending from a proximal insulator end to a distal insulator end, and a sealing collar extending radially outward from the insulator wall at the distal insulator end, and further comprising:

mounting an electrode within an insulator channel of the insulator such that the insulator wall is between the electrode and the mounting wall.

20. The method of claim 17, wherein the fixation helix includes a helix revolving about the longitudinal axis.

* * * * *